(12) United States Patent
Yan et al.

(10) Patent No.: US 11,235,011 B2
(45) Date of Patent: *Feb. 1, 2022

(54) USE OF ALPHAVIRUS IN PREPARATION OF ANTITUMOR DRUGS

(71) Applicant: GUANGZHOU VIROTECH PHARMACEUTICAL CO., LTD, Guandong (CN)

(72) Inventors: Guangmei Yan, Guangzhou (CN); Xiao Xiao, Guangzhou (CN); Jun Hu, Guangzhou (CN); Kai Li, Guangzhou (CN); Jiankai Liang, Guangzhou (CN); Yuan Lin, Guangzhou (CN); Haipeng Zhang, Guangzhou (CN); Suizhen Lin, Guangzhou (CN)

(73) Assignee: GUANGZHOU VIROTECH PHARMACEUTICAL CO., LTD., Guangzhou (CN)

( * ) Notice: Subject to any disclaimer, the term of this patent is extended or adjusted under 35 U.S.C. 154(b) by 76 days.

This patent is subject to a terminal disclaimer.

(21) Appl. No.: 16/680,885

(22) Filed: Nov. 12, 2019

(65) Prior Publication Data
US 2020/0085892 A1 Mar. 19, 2020

Related U.S. Application Data

(63) Continuation of application No. 15/118,375, filed as application No. PCT/CN2015/087945 on Aug. 24, 2015, now Pat. No. 10,517,909.

(30) Foreign Application Priority Data

Aug. 26, 2014 (CN) .......................... 201410425510.3

(51) Int. Cl.
| | | |
|---|---|---|
| A61K 35/768 | (2015.01) | |
| A61K 39/00 | (2006.01) | |
| A61K 31/404 | (2006.01) | |
| A61K 31/427 | (2006.01) | |
| A61K 31/713 | (2006.01) | |
| C12N 7/00 | (2006.01) | |
| C12N 15/113 | (2010.01) | |

(52) U.S. Cl.
CPC .............. *A61K 35/768* (2013.01); *C12N 7/00* (2013.01); *C12N 15/1138* (2013.01); *C12N 2310/14* (2013.01); *C12N 2320/31* (2013.01); *C12N 2770/36132* (2013.01)

(58) Field of Classification Search
CPC .............. A61K 2300/00; A61K 35/768; A61K 31/404; A61K 31/427; A61K 31/713
See application file for complete search history.

(56) References Cited

U.S. PATENT DOCUMENTS

2004/0127453 A1  7/2004  Lyons et al.
2012/0275999 A1  11/2012  Bell et al.

FOREIGN PATENT DOCUMENTS

| CN | 102026645 A | 4/2011 |
|---|---|---|
| CN | 102858959 A | 1/2013 |
| CN | 104138375 A | 11/2014 |
| CN | 104814984 A | 8/2015 |
| WO | 0011201 A1 | 3/2000 |
| WO | 2007/050074 A1 | 5/2007 |
| WO | WO2007050074 | * 5/2007 |
| WO | 2009/033490 A1 | 3/2009 |
| WO | 2010151773 A2 | 12/2010 |

OTHER PUBLICATIONS

Hu et al. "Alphavirus M1 induces apoptosis if malignant glioma cells via downregulation and nucleolar translocation", Cell Cycle, 2009, 8(20);3328-3339.*
Salvetti et al. "Viruses and the nucleolus; the fatal attraction", Biochemica et biophysica acta, 2014;840-847.*
Communication, dated Sep. 19, 2019, issued by the Indian Patent Office in Indian Application No. 201617026172.
Communication, dated Apr. 14, 2019, issued by the Israeli Patent Office in counterpart application No. 247082.
Communication, dated Apr. 24, 2019, issued by the Canadian Intellectual Property Office in counterpart application No. 2,939,535.
Communication, dated Apr. 18, 2019, issued by the State Intellectual Property Office of the P.R.C. in counterpart Chinese application No. 201710516707.1.
Communication, dated Apr. 18, 2019, issued by the State Intellectual Property Office of the P.R.C. in counterpart Chinese application No. 201710666533.7.
Communication, dated Jun. 14, 2019, issued by the New Zealand Intellectual Property Office in counterpart application No. 746338.
Communication, dated Jun. 17, 2019, issued by the European Patent Office in counterpart application No. 15 835 808.5.
Wen, J-S. et al., "Genomic analysis of a Chinese isolate of Getah-like virus and its phylogenetic relationship with other Alphaviruses", Virus Genes, 2007, 35: 597-603.
Barth R. F. et al.; "Rat brain tumor models in experimental neuro-oncology: the C6, 9L, T9, RG2, F98, BT4C, RT-2 and CNS-1 gliomas", Journal of Neuro-Oncology, 2009; 94(3): 299-312.
Communication dated Oct. 31, 2018 from the Russian Patent and Trademark Office in counterpart application No. 2016131756/04.
Communication dated May 7, 2018 from the Canadian Intellectual Property Office in counterpart application No. 2,939,535.

(Continued)

*Primary Examiner* — Barry A Chestnut
(74) *Attorney, Agent, or Firm* — Sughrue Mion, PLLC

(57) ABSTRACT

Disclosed is use of alphavirus in preparation of antitumor drugs. The alphavirus is M1 virus or Getah virus. In addition, the specific tumor types sensitive to abovementioned alphavirus treatment are further determined, so as to provide a safe and effective solution for antitumor drug administering schemes.

20 Claims, 5 Drawing Sheets
(1 of 5 Drawing Sheet(s) Filed in Color)
Specification includes a Sequence Listing.

(56) References Cited

OTHER PUBLICATIONS

Communication, dated Dec. 13, 2017, issued by the European Patent Office in European counterpart application No. 15835808.5.
Communication, dated May 7, 2018, issued by the New Zealand Intellectual Property Office in New Zealand counterpart application No. 722768.
Communication, dated May 8, 2018, issued by the Japanese Patent Office in Japanese counterpart application No. 2016-550515.
Communication, dated Mar. 27, 2018, issued by the Korean Intellectual Property Office in Korean counterpart application No. 10-2016-7021337.
Communication, dated Jul. 26, 2018, issued by the Korean Intellectual Property Office in Korean counterpart application No. 10-2016-7021337.
Communication, dated Jan. 12, 2018, issued by the Russian Patent and Trademark Office in Russian counterpart application No. 2016131756/15(049314).
Communication, dated Jun. 7, 2018, issued by the Russian Patent and Trademark Office in Russian counterpart application No. 2016131756/15(049314).
Cai, Qiu-Yan, et al., "Current status of gene therapy vector research." International Journal Biologicals, Feb. 2011, vol. 34, No. 1, pp. 26-29, Department of Blood Transfusion, Anhui Provincial Hospital, Anhui Medical University, Heifei 230000, China.
Dong, Zhiqiang et al., "Expressions of 21 and survivin proteins in glioma tissue and their clinical significances." Journal of Jilin University (Medical Edition), Sep. 2015, vol. 41, No. 5, pp. 1004-1007, Department of Neurosurgery, Second Hospital, Lanzhou University, Lanzhou 730030, China.
Weaver, Scott C., et al., "Venezuelan equine encephalitis." Annual Reviews in Entomology Aug. 14, 2003, vol. 49, No. 1, pp. 141-174, Center for Biodefense and Emerging Infectious Diseases and Department of Pathology, University of Texas Medical Branch, Galveston, Texas 77555-0609; Instituto Nacional de Salud, Avenida Eldorado, Carrera 50, Apartado 80080, Bogotá, Colombia; Instituto de Zoologia Tropical, Laboratorio de Biolog'ia de Vectores, Universidad Central de Venezuela, 1041-A, Apartado 47058, Caracas, Venezuela.
Ibraheem, D., et al., "Gene therapy and DNA delivery systems." International journal of pharmaceutics, Jul. 24, 2013, vol. 459, pp. 70-83, University of Lyon, F-69622, Lyon; University of Lyon-1, Villeurbanne, France.
Cao, Y., et al., "Clinical tolerance trial on recombinant human endostatin adenovirus." Chinese journal of cancer, 2007, vol. 26, No. 8, pp. 856-860, State Key Laboratory of Oncology in South China, Guangzhou, Guangdong, 510060, P. R. China; Department of Medical Oncology, Cancer Center, Sun Yat-sen University, Guangzhou, Guangdong, 510060, P. R. China; Research Department, Cancer Center, Yat-sen University, Guangzhou, Guangdong, 510060, P. R. China.
Quetglas, Jose I., et al., "Alphavirus vectors for cancer therapy." Virus research, 2010, vol. 153, No. 2, pp. 179-196, Division of Gene Therapy, School of Medicine, Center for Applied Medical Research (CIMA), University of Navarra, Av. Pio XII 55, 31008 Pamplona, Spain.
Zhang, Yong-Qiang, et al., "The Progress of Investigation of Animal Models of C6 Glioma." Guangzhou Chemical Industry, Mar. 2014, vol. 42, No. 6, Anhui University of Chinese Medicine, Anhui Hefei 230001, China; Anhui Provincial Hospital, Anhui Hefei 230001, China.
Hu et al., "Alphavirus M1 induces apoptosis of malignant glioma cells via downregulation and nucleolar translocation", Cell Cycle, 2009, 8(20);3328-3339.
Wang, Xiao-Wu, et al., "Establishment and Comparison of Sprague-Dawley Rats and Wistar Rats of Cerebral Glioma Model." Chinese Journal of Comparative Medicine, May 2010, vol. 20, No. 5, pp. 8-11, Department of Radiation Medicine, Faculty of Preventive Medicine, Xi'an 710032, China; Department of Radiology, The Fourth Military Medical University, Xi'an 710031, China.
Piccolo, Maria Teresa, et al., "The dual role played by p21 may influence the apoptotic or anti-apoptotic fate in cancer." Journal of Cancer Research Updates, 2012, vol. 1, No. 2, 189-202, Gene Expression & Human Molecular Genetics Laboratory, Institute of Genetics and Biophysics "A.B.T." CNR, Naples, Italy; National Institute of Biostructures and Biosystems, Rome, Italy.
Wang, Zhan-Xiang, et al., "Effects of exogenous p21WAFI/CIPI gene on the growth and cell cycle of human glioma cells" Journal Fourth Military Medicine University, 2003, vol. 22, No. 24, pp. 2030-2033, PLA Institute of Neurosurgery, Xijing Hospital, Fourth Military Medical University, Xi'an 710033, China.
Song, Tao, et al., "Correlation analysis between the expression of P21WAF1/CIP1, P16 proteins and human glioma." Clinical and experimental medicine, 2008, vol. 8, No. 3, pp. 151-157, Neurosurgery Department, Xiangya Hospital of Central South University, Changsha, Hunan, P.R. China 410078; Cardiology Department, Xianga Hospital of Central South University, Changsha, Human, P.R. China.
International Search Report, dated Nov. 19, 2015, issued by the International Bureau in counterpart International Application No. PCT/CN2015/087945.
Lin, Yuan et al.; "Identification and Characterization of Alphavirus M1 as a Selective Oncolytic Virus Targeting ZAP-defective Human Cancers", PNAS, Oct. 6, 2014 (Oct. 6, 2014), E4504-E4512.
Salvetti, A. et al.; "Viruses and the Nucleolus: The Fatal Attraction", Biochimica Et Biophysica Acta, No. 1842, Dec. 27, 2013 (Dec. 27, 2013), pp. 840-847.
Communication, dated Aug. 5, 2016, issued by the Australian Intellectual Property Office in counterpart application No. 2015309403.
David M. Knipe & Peter M. Howley, "Fields Virology," 6th edition, 2013, Chapter 23, Alphaviruses: 136 pages total.
Communication, dated Aug. 25, 2016, issued by the State Intellectual Property Office of the P.R.C. in counterpart Chinese Patent Application No. 201410425510.3.
Communication, dated Jun. 15, 2017, issued by the State Intellectual Property Office of the P.R.C. in counterpart Chinese Patent Application No. 201410425510.3.
Communication, dated Jan. 15, 2016, issued by the State Intellectual Property Office of the P.R.C. in counterpart Chinese Patent Application No. 201410425510.3.
Communication, dated May 25, 2016, issued by the State Intellectual Property Office of the P.R.C. in counterpart Chinese Patent Application No. 201410425510.3.
Communication, dated Jul. 17, 2017, issued by the Canadian Patent Office in counterpart Canadian Patent Application No. 2939535.
Communication, dated Oct. 3, 2017, issued by the Japanese Patent Office in counterpart Japanese Patent Application No. 2016-550515.
Communication, dated Jul. 11, 2017, issued by the Korean Intellectual Property Office in counterpart Korean Patent Application No. 10-2016-7021337.
Communication, dated Sep. 15, 2017, issued by the New Zealand Patent Office in counterpart New Zealand Patent Application No. 722768.
Communication, dated Jul. 7, 2017, issued by the Singapore Patent Office in counterpart Singapore Patent Application No. 11201606707R.
Communication, dated Nov. 23, 2016, issued by the Taiwanese Patent Office in counterpart Taiwanese Patent Application No. 104127467.
Bick, M., et al., "Expression of the Zinc-Finger Antiviral Protein Inhibits Alphavirus Replication", Journal of Virology, vol. 77, No. 21, Nov. 2003, p. 11555-11562 (8 pages).
Mao, R., et al., "Inhibition of Hepatitis B Virus Replication by the Host Zinc Finger Antiviral Protein", PLOS Pathogens, Jul. 2013, vol. 9, Issue 7, e1003494, pp. 1-18 (18 pages).
Communication, dated Jul. 21, 2017, issued by the Taiwanese Patent Office in counterpart Taiwanese Patent Application No. 104127467.
Result of Consultation of counterpart application EP 15835808.5 Nov. 28, 2019.
1st Adverse Report of counterpart Malaysian application No. PI2016702817 Oct. 30, 2019.
2nd Adverse Report of counterpart Malaysian application No. PI2016702817 Jan. 21, 2021.
2nd Office Action of counterpart Israeli application No. 247082 dated Sep. 1, 2020.

(56) References Cited

OTHER PUBLICATIONS

1st Office Action of counterpart Mexican application No. MX/a/2016/010058 dated Jul. 24, 2020.
Hearing Notice of counterpart Indian application No. 201617026172 Dec. 7, 2020.
3rd Office Action of counterpart Chinese continuation application No. 201710516707.1 dated Apr. 9, 2020.
3rd Office Action of counterpart Chinese continuation application No. 201710666533.7 dated Apr. 9, 2020.
Decision of Refusal of counterpart Chinese continuation application No. 201710666533.7 dated Oct. 30, 2020.
Non-Final Notice of Reasons for Refusal of counterpart Japanese continuation application No. 2018-218457 dated Nov. 26, 2019.
Decision of Refusal of counterpart Japanese continuation application No. 2018-218457 dated Jul. 14, 2020.

* cited by examiner

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
gatcattgct cctcctgagc                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
actcctgctt gctgatccac                                                   20

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
gttccaacag gcgtcaccat c                                                 21

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
acacattctt gtctagcaca gtcc                                              24

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
tcacgaactc tctggactga a                                                 21

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
acttttgcat atctcgggca taa                                               23

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
ccaagagtag cacttgtta                                                    19

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

```
<400> SEQUENCE: 8
ccaagaguag cacuuguuat t                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
uaacaagugc uacucuuggt t                                               21
```

USE OF ALPHAVIRUS IN PREPARATION OF ANTITUMOR DRUGS

This is a continuation of U.S. patent application Ser. No. 15/118,375, filed Aug. 11, 2016, (now allowed), which was the National Stage of International Application No. PCT/CN2015/087945, filed Aug. 24, 2015, claiming priority based on Chinese Patent Application No. 201410425510.3, filed Aug. 26, 2014, the contents of all of which are incorporated herein by reference in their entirety.

TECHNICAL FIELD

The present disclosure belongs to the technical field of biomedicine, and it relates to use of alphavirus in preparation of antitumor drugs.

BACKGROUND OF THE DISCLOSURE

Tumors derive from accumulative change of genes and epigenetics in normal cells, such change promotes conversion of normal cells into malignant tumors. This complex pathological change process determines diversity of mechanisms of genesis, maintenance and metastasis in different tumors. At present, surgical excision, chemotherapy and radiotherapy are common methods for clinical therapy of tumors, however surgical excision of tumors is prone to recur, and toxic and side effects of the radiotherapy and the chemotherapy are obvious.

15-20% of human cancers are associated with viral infection, for example, hepatitis B virus (HBV) and hepatitis C virus (HCV) are associated with liver cancers, and human papillomavirus (HPV) is associated with cervical cancers, etc.

Alphavirus belongs to Togaviridae, and it is a type of single stranded RNA virus with an envelope structure, transmitted mainly by a transmission media of arthropod. 13 in 29 types of alphaviruses can cause diseases of human and animals (David M. Knipe, Peter M. Howley, Chapter 23, Alphaviruses, Fields Virology 6$^{th}$ edition: 651-685, 2013).

Venezuelan equine encephalitis virus of alphaviruses can act as a vector to transduce dendritic cells so as to treat tumors (Moran T P, Burgents J E, Long B, et al: Alphaviral vector-transduced dendritic cells are successful therapeutic vaccines against neu-overexpressing tumors in wild-type mice. Vaccine 25: 6604-6612, 2007). However, such virus had induced fever, convulsion, abortion and even death of human, thus selectivity and safety problems severely affect use of the virus in antitumor therapy.

SUMMARY OF THE DISCLOSURE

A purpose of the present disclosure is to provide a safe and effective viral antitumor drug.

A further purpose of the present disclosure is to provide a safe and effective viral antitumor drug against a specific tumor type.

A further purpose of the present disclosure is to provide a safe and effective viral antitumor drug against a specific individual/tumor.

A further purpose of the present disclosure is to provide an effective antitumor administrating system and administrating method.

A further purpose of the present disclosure is to provide a more effective antitumor drug and a tumor treatment method.

The above-mentioned purposes are achieved by the present disclosure via the following technical solution.

The present disclosure provides use of alphavirus in preparation of antitumor drugs, wherein the alphavirus is M1 virus or Getah virus.

M1 virus (Alphavirus M1) belongs to Alphavirus, and it was isolated from *Culex* mosquitos in Hainan Island, China in 1964 (Li X D, et al: Isolation of Getah virus from mosquitos collected on Hainan Island, China, and results of a serosurvey. Southeast Asian J Trop Med Public Health 23: 730-734, 1992.). Complete genomic sequence of M1 virus was determined in 2008 (Zhai Y G, et al: Complete sequence characterization of isolates of Getah virus (genus Alphavirus, family Togaviridae) from China. J Gen Virol 89: 1446-1456, 2008.). Its acquisition method is optional but not limited to the acquisition by the method in the above-mentioned literatures, or by the following deposit information (deposit number: CCTCC V201423; deposit time: Jul. 17, 2014; Classification and nomenclature: Alphavirus M1; depositary institution: China Center for Type Culture Collection; deposit address: Wu Han University in Luo Jia Shan, Wuchang District, Wuhan, Hubei Province).

The results of the previous researches on M1 virus by researchers of the present disclosure indicated that M1 virus had a killing effect against some tumor cells, such as rat malignant glioma cell C6, human malignant glioma cell U251 and U-87; however, it was not effective in killing some other tumor cells, such as human malignant glioma cell T98G. These researches cannot confirm that M1 virus has an effective antitumor effect.

The present disclosure further provides tumor types to which the virus is more applicable, in order to improve the therapy efficacy when M1 virus is used as the antitumor drug.

More preferably, the present disclosure using M1 virus as the antitumor drugs is effective in treating one or more of liver cancer, colorectal cancer, bladder cancer, breast cancer, cervical cancer, prostate cancer, glioma, melanoma, pancreatic cancer, nasopharyngeal carcinoma, lung cancer, and gastric cancer.

The inventors found that M1 virus causes varying degrees of cell death for various tumor cells. After 48 hours of M1 virus treatment of the tumor cells (MOI=10), the cell death rates of pancreatic cancer, nasopharyngeal carcinoma, prostate cancer and melanoma are more than 50%; the cell death rates of colorectal cancer (LoVo, HCT-8, SW620 and SW480), liver cancer (Hep3B, Huh-7 and Huh-6), bladder cancer and breast cancer are more than 40%; the cell death rates of glioma, cervical cancer, lung cancer are more than 30%; the cell death rate of gastric cancer is more than 20%. The above-mentioned results suggest that the M1 virus as an antitumor drug has the most significant effects on such tumor types: pancreatic cancer, nasopharyngeal carcinoma, prostate cancer and melanoma; while following are tumor types of colorectal cancer, liver cancer, bladder cancer and breast cancer; while further following are tumor types of glioma, cervical cancer, lung cancer; while least significant effects occur with the tumor type of gastric cancer.

Because M1 virus belongs to Getah-like virus and its homology with Getah virus is up to 97.8%, a person skilled in the art have a reason to recognize that, on basis of antitumor effect of M1 virus, Getah virus also has a similar action and effect as M1 virus.

Further, the present disclosure provides a method for more accurately and effectively providing a therapeutic scheme and a therapeutic drug against a specific individual/tumor, as well as an associated drug against the specific individual/tumor.

The inventors first found that the virus was suitable for treating ZAP low expression tumors or ZAP negative tumors, preferably for treating ZAP low expression solid tumor or ZAP negative solid tumor.

It found that the efficacy of M1 virus therapy against tumor is closely related to the ZAP expression regulation of the tumor. The replication of M1 virus is inhibited by ZAP which is low expressed or negative in various tumor types. M1 virus can selectively treat ZAP low expression or ZAP negative tumors/individual.

ZAP is an abbreviation of zinc Finger CCCH-type antiviral protein 1, its English name is zinc finger CCCH-type antiviral protein 1, and it is encoded by zc3hav1 gene. It is reported that, in cells ZAP inhibits replication of certain viruses, such as Ebola virus and Marburg virus, by mechanism of inducing RNA degradation and translation inhibition. However, ZAP has no inhibitory effect on replication of other viruses, such as vesicular stomatitis virus, poliovirus and yellow fever virus, etc.

The inventors found that M1 virus can significantly cause cell death in ZAP low expression/ZAP negative cell lines, and M1 virus was enriched in ZAP low expression/ZAP negative tumor tissues of a tumor-bearing animal body, inhibiting tumor growth. In the meanwhile M1 virus inhibits survival of ZAP low expression/ZAP negative human ex vivo living tumor tissues.

The inventors found for the first time that in different multiple types of tumors, expression level of ZAP in tumor tissues is lower than that in paracancerous non-neoplastic tissues. Immunohistochemical analysis on various types of clinical tumor pathological specimens indicated that, in 69% of liver cancer tissues, 52% of the colorectal cancer tissues and 61% of the bladder cancer tissues, ZAP expression levels are significantly lower than that in the corresponding paracancerous non-neoplastic tissues. M1 virus can be used for selectively treating ZAP low expression/ZAP negative tumors.

The experiment results proved for the first time that replication of M1 virus was inhibited by ZAP, and ZAP expression level was the decisive factor influencing the M1 virus' effect of selective tumor cell death induction and tumor growth inhibition. The inventors found that antitumor effect of M1 virus was directly related to the expression level of ZAP. The inventors found that, if the tumor cells with knockdown of ZAP were infected with M1 virus, the survival rate of the tumor cells was significantly decreased compared with the tumor cells without knockdown of ZAP. Thus, as an optional preferred therapeutic scheme, when a cancer patient is treated with M1 viral, a ZAP inhibitor can be administrated at the same time or in advance, in order to improve sensitivity of tumor to M1 virus.

Therefore, in order to further improve therapy efficacy of M1 virus as an antitumor drug, when adopting a therapeutic scheme, the ZAP expression in tumor can be firstly determined for the patient, then the therapeutic scheme using M1 virus can be specifically administrated, thereby improving the efficacy of the therapeutic scheme, and avoiding time delay due to ineffective administration and avoiding drug abuse. For example, the tumor ZAP expression of the patient is firstly detected before administration, and if the tumor is of ZAP low expression or ZAP negative expression, the M1 viral therapy can be directly provided; if the tumor is of ZAP normal expression/ZAP high expression, a ZAP inhibitor can be provided before or at the same time during the administration of the M1 virus, thereby improve sensitivity of the tumor to M1 virus, and improve the therapy efficacy. Said ZAP inhibitor is for example, ZAP expression or function inhibitor, ZAP interference fragment, or ZAP antibody, etc. ZAP expression quantity in the tumor directly affects the efficacy of the M1 therapy. The lower ZAP expression quantity of the tumor is, the more effective it is to be treated by M1. To determine whether a certain individual/tumor is suitable for M1 treatment or not, tumor ZAP expression level can firstly be detected. Preferably, ZAP expression level can be determined by, but not limited to the following means:

Low or high expression of ZAP refers to conclusion obtained by comparison of ZAP mRNA or protein quantity between two groups of specimens or two specimens. If the ZAP mRNA or protein quantity of one group of specimens or one specimen is less than or more than that of the other group of specimens or the other specimen, this specimen is called ZAP low or high expression, respectively; ZAP negative refers those totally with no expression of ZAP mRNA or protein. Sets of specimens used for comparison of ZAP mRNA and protein quantity can be: tumor cells vs. normal cells, tumor tissues vs. paracancerous non-neoplastic tissues, or tumors effective to M1 treatment vs. tumors that are not effective to M1 treatment.

As an optional means, ZAP high, low or negative expression in the tumors means that, the quantity of ZAP mRNA and protein of the tumor tissues is more, less or no expression, respectively, compared with that of the corresponding paracancerous non-neoplastic tissues. If the normalized expression quantity of ZAP mRNA or protein of the former one (tumor tissues) is less than that of the latter one (paracancerous non-neoplastic tissues), in other word, if the ratio of the ZAP normalized expression quantity of the tumor tissues to that of the paracancerous non-neoplastic tissues is <1, it belongs to ZAP low expression, and thus is suitable to be treated by M1. More effectively, the therapy object is a tumor in which the ratio of ZAP normalized expression quantity of the tumor tissues to that of the paracancerous non-neoplastic tissues is <0.8, more preferably <0.6, more preferably <0.4, more preferably <0.3, more preferably <0.2, more preferably <0.1, and most preferably, the tumor tissue is ZAP negative. These tumor tissues and the corresponding paracancerous non-neoplastic tissues include, but not limited to, tissue specimens obtained from pathological puncture or surgical resection. Clinical investigation found that, in certain tumor tissues, ZAP expression quantity is even higher than that in the paracancerous non-neoplastic tissue, and these tumors or tumor patients will not be suitable for a direct administration of M1 for therapy. The detection method for ZAP mRNA or protein includes but not limited to QRT-PCR, Northern Blot, Western Blot, immunohistochemistry, ELISA, etc. To accurately determine the difference of ZAP mRNA or protein quantity between different specimens, the normalized expression quantity of ZAP mRNA or protein in each specimen are firstly calculated. The normalized expression quantity refers to that ZAP mRNA or protein expression value of each specimen is divided by mRNA or protein expression value of a internal reference of the specimen, and a normalized analysis is conducted to obtain a ZAP normalized expression quantity of the specimen. In different detection methods, the internal references can be different, and their common characteristics is that the internal reference expression quantities in different cells or tissue specimens are identical, therefore ZAP expression quantities of different specimens through such normalized analysis are comparable, so as to determine the quantity difference of ZAP mRNA or protein between the specimens.

In one exemplary example of the present disclosure (FIG. 4), for the growth inhibition effects of M1 against human ex vivo cultivated living liver cancer tissues and colorectal cancer tissues, different inhibition results are obtained between the two kinds of tissues (Table 2 and Table 3), wherein in total up to 32 specimens present a tumor growth inhibition rate of more than 10%, while 19 specimens present a tumor growth inhibition rate of less than or equal to 10%. The expression levels of ZAP and internal reference mRNA of each tumor tissue in these two groups are further analyzed by QRT-PCR method (respectively $2^{-Ct\ value}$), and $2^{-Ct\text{-}ZAP}$ of each specimen is divided by $2^{-Ct\text{-}internal\ reference}$ to obtain respective ZAP normalized expression quantity. Based on a statistical analysis of ZAP normalized expression quantity of the specimens in the above-mentioned two groups, it is found that the ZAP normalized expression quantity of the specimen group with an inhibition rate of more than 10% is 0.117±0.890, it is lower than the group with an inhibition rate of less than or equal to 10% (0.791±0.108), and the ratio of these two mean value is 0.148.

As another optional method, ZAP high, low or negative expression of the tumor means that the quantity of ZAP mRNA and protein of the tumor cells (e.g., derived from tumor patient's cultured tumor cells) is more, less or no expressed, compared with those of normal cells. If the ZAP mRNA or protein normalized expression quantity of the former is less than that of the latter (i.e., the ratio of ZAP normalized expression quantity of the tumor cells to that of the normal cells is <1), it belongs to ZAP low expression, and it is suitable for a therapy with M1. A more effective therapy object is a tumor in which the ratio of ZAP normalized expression quantity of the tumor cells to that of the normal cells is <0.8, more preferably <0.6, more preferably <0.4, more preferably <0.3, more preferably <0.2, more preferably <0.1, and most preferably, the tumor cell is ZAP negative.

In an exemplary example of the present disclosure (FIG. 3c), difference of ZAP protein expression level between HepG2 liver cancer cell line and L-02 normal liver cell line is detected by Western Blot method, meanwhile a standard reference β-actin whose expression quantity is identical between different specimens is detected, wherein grey scale of Western blot detection band represents the quantity of the detected molecules. The ZAP normalized protein expression quantity=(ZAP band grey scale mean value)/(β-actin band grey scale mean value). The ratio of ZAP normalized protein expression quantity of HepG2 to those of L-02 is 0.8, ZAP is low expressed in Hep G2. After infection with the M1 virus, the survival rate of the Hep G2 cell is only 70.4%±3.5%, while the survival rate of L-02 under same treatment is 100.3±10.0%, the difference of survival rate between them is of statistical significance.

In another exemplary example (FIG. 3a and FIG. 3b), for ZAP of tumor cell lines T24, SCaBER, LoVo and Hep3B, the mRNA (FIG. 3a) and protein (FIG. 3b) are detected by QRT-PCR and Western blot, and then compared with respective internal references, to obtain the normalized expression quantity which is undetectable or close to 0 (<0.1), that is to say, the ZAP expression is negative or close to negative (<0.1); after these tumor cells are infected by M1, cell death is induced, and the cell survival rate is significantly reduced to: T24 21.1%, SCaBER 11.5%, LoVo 6.9% and Hep3B 3.8% (Table 1). For the normal cell L-02 and HEB as shown in FIG. 3a and FIG. 3b, the ratio of the normalized expression quantity of ZAP mRNA (FIG. 3a) or protein to that of the above-mentioned tumor cell is more than 1, which belongs to ZAP high expression, and after M1 infection no obvious reduction of survival rate of these normal cells is induced. The survival rate of L-02 is 100.3%, and that of HEB is 98.8% (Table 1).

Thereby, the present disclosure also provides an antitumor administrating system, characterized in that, it comprises a ZAP expression level detecting reagent, and alphavirus; the alphavirus is M1 virus or Getah virus. The tumor ZAP expression level of the patient is firstly detected, then a suitable administration scheme is specifically adopted.

The present disclosure also provides an antitumor drug, comprising alphavirus and ZAP inhibitor; the alphavirus is M1 virus or Getah virus. The ZAP inhibitor is ZAP expression or function inhibitor, ZAP interference fragment, or ZAP antibody, etc.

In order to avoid killing effect of M1 virus to normal cells, preferably, the ZAP inhibitor is specifically provided or targeted to the tumor tissues, being a tumor targeted ZAP inhibitor.

As an optional embodiment, antitumor drug provided by the present disclosure can be injectio, tablet, capsule, or patch, etc. As a preferred embodiment, the antitumor drug of the present disclosure is injectio; preferably, intravenous injection is conducted.

As an optional administration means, the M1 virus of the present disclosure can be administered by intravenous or intratumoral injection. In the intratumoral injection, $2 \times 10^5$ PFU/kg-$2 \times 10^9$ PFU/kg is administrated every day; in the intravenous injection, $2 \times 10^6$ PFU/kg-$2 \times 10^{10}$ PFU/kg is administrated every day. Compared with the solvent control group, the M1 virus group significantly inhibited the growth of tumors.

Compared with the prior art, the present disclosure has the following beneficial effects:

The antitumor drugs provided by the present disclosure may be used for treating various types of tumors including liver cancer, colorectal cancer, bladder cancer, breast cancer, cervical cancer, prostate cancer, glioma, melanoma, pancreatic cancer, nasopharyngeal carcinoma, lung cancer, and gastric cancer. Cytology experiments prove that M1 virus causes death of various types of tumor cells; animal experiments prove that M1 virus in vivo significantly inhibits growth of liver cancer and colorectal cancer; human ex vivo living tumor tissue culture experiments prove that M1 virus significantly inhibits survival of liver cancer and colorectal cancer tissues.

The antitumor drugs provided by the present disclosure can preferentially treat ZAP low expression/ZAP negative tumors, including but not limited to liver cancer, colorectal cancer, bladder cancer, breast cancer, cervical cancer, prostate cancer, glioma, melanoma, pancreatic cancer, nasopharyngeal carcinoma, lung cancer, and gastric cancer.

The antitumor drug provided by the present disclosure has selective antitumor activity, with good safety. M1 virus can selectively cause tumor cell death, but it has no effect on survival of the normal cells, indicating that M1 virus has tumor cell selectivity. In tumor-bearing nude mouse body, the M1 virus intravenously injected is highly enriched in the tumor tissues, while the virus quantity existed in the normal tissues is lower, and the difference of the virus quantity between the above said two kinds of tissues is about $10^2$-$10^6$ times. This further proves that M1 virus selectively affect tumor. In addition, the administration of the M1 virus does not affect body weight and mental status of the nude mouse, indicating that the M1 virus is with good safety.

The present disclosure for the first time provides a safe and effective viral antitumor drug against specific individual/tumor. The drug of the present disclosure selectively treats ZAP low expression/ZAP negative tumors, thereby increasing dosage effective rate, avoiding ineffective administration and drug abuse.

The present disclosure provides a more effective administrating method and administrating system. The ZAP expression level of the patient tumor is detected firstly, then a drug therapy is specifically provided, or assisted by other means to provide a therapy, thereby improving specificity and efficacy of the M1 virus therapy.

The present disclosure provides a more effective antitumor drug and tumor therapeutic method; a ZAP inhibitor is supplemented before administration or at the same time of administration, thereby improving sensitivity of the tumors to the drug.

BRIEF DESCRIPTION OF THE DRAWINGS

The patent or application file contains at least one drawing executed in color. Copies of this patent or patent application publication with color drawings will be provided by the office upon request and payment of the necessary fee.

a) shows that M1 virus infection causes cytomorphological change of the tumors;

b) shows that M1 virus infection has no effect on morphology of normal cell lines, Control represents a control group of OptiPRO™ SFM medium, M1 represents an experiment group of M1 virus infection.

Figure 2:
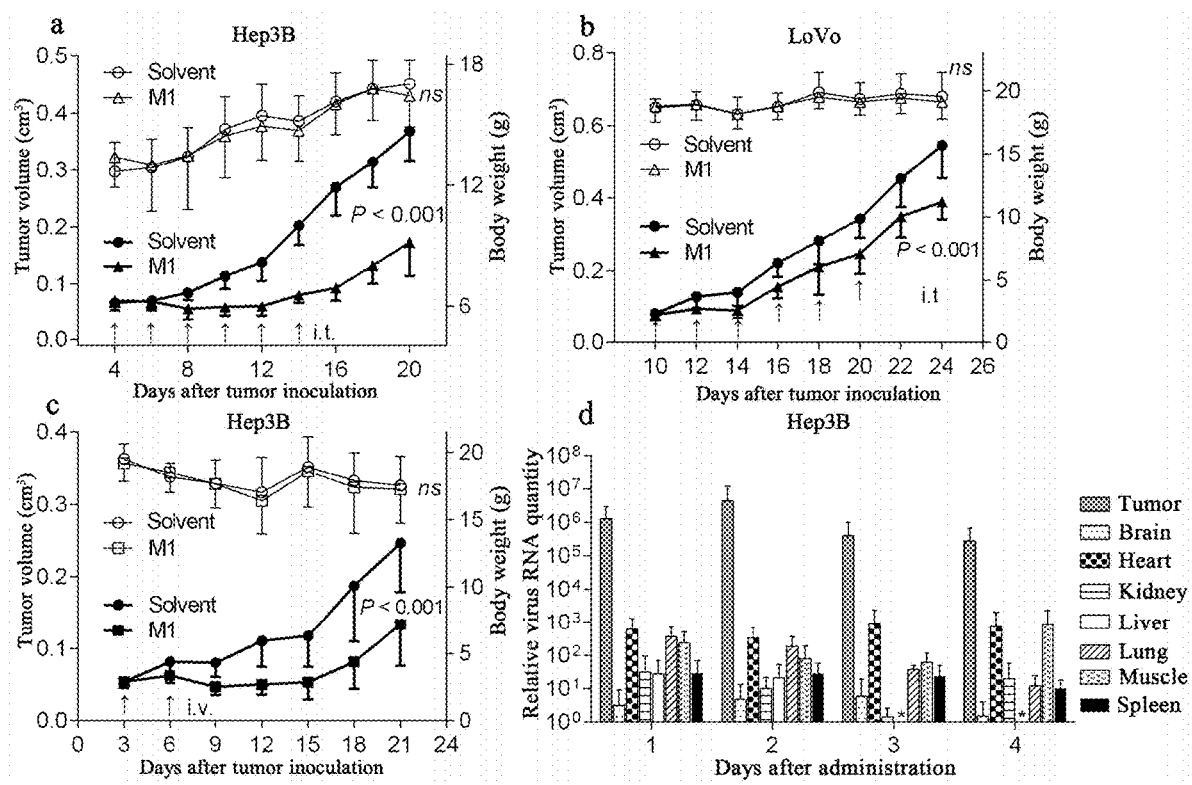

FIG. 2 shows that M1 virus effectively inhibits tumor growth of a tumor-bearing mice;

a) shows the influence of M1 virus on the tumor volume and animal body weight of a Hep3B tumor-bearing mice after treated with intratumoral injection of M1, wherein M1 represents M1 virus treated group, solvent represents a control group of OptiPRO™ SFM medium solvent, (n=9);

b) shows influence of M1 virus on tumor volume and animal body weight of a LoVo tumor-bearing mice after treated with intratumoral injection of M1, (n=11);

c) shows influence of M1 virus on tumor volume and animal body weight of Hep3B tumor-bearing mice after treated with intravenous injection of M1, (n=9);

d) shows tissue distribution of M1 in the Hep3B tumor-bearing mice after treated with intravenous injection of the M1 virus. QRT-PCR detection is conducted (n=6);

The data of the tumor volume and body weight are represented by mean value±standard deviation, and the statistical method is ANOVA method; the arrows represent for M1 virus treated group, the circles represent for the control group of OptiPRO™ SFM medium, ns represents for no statistical difference; i.t represents for intratumoral injection, i.v represent for intravenous injection; and * represents that on mRNA expression of M1 virus is detected.

Figure 3:
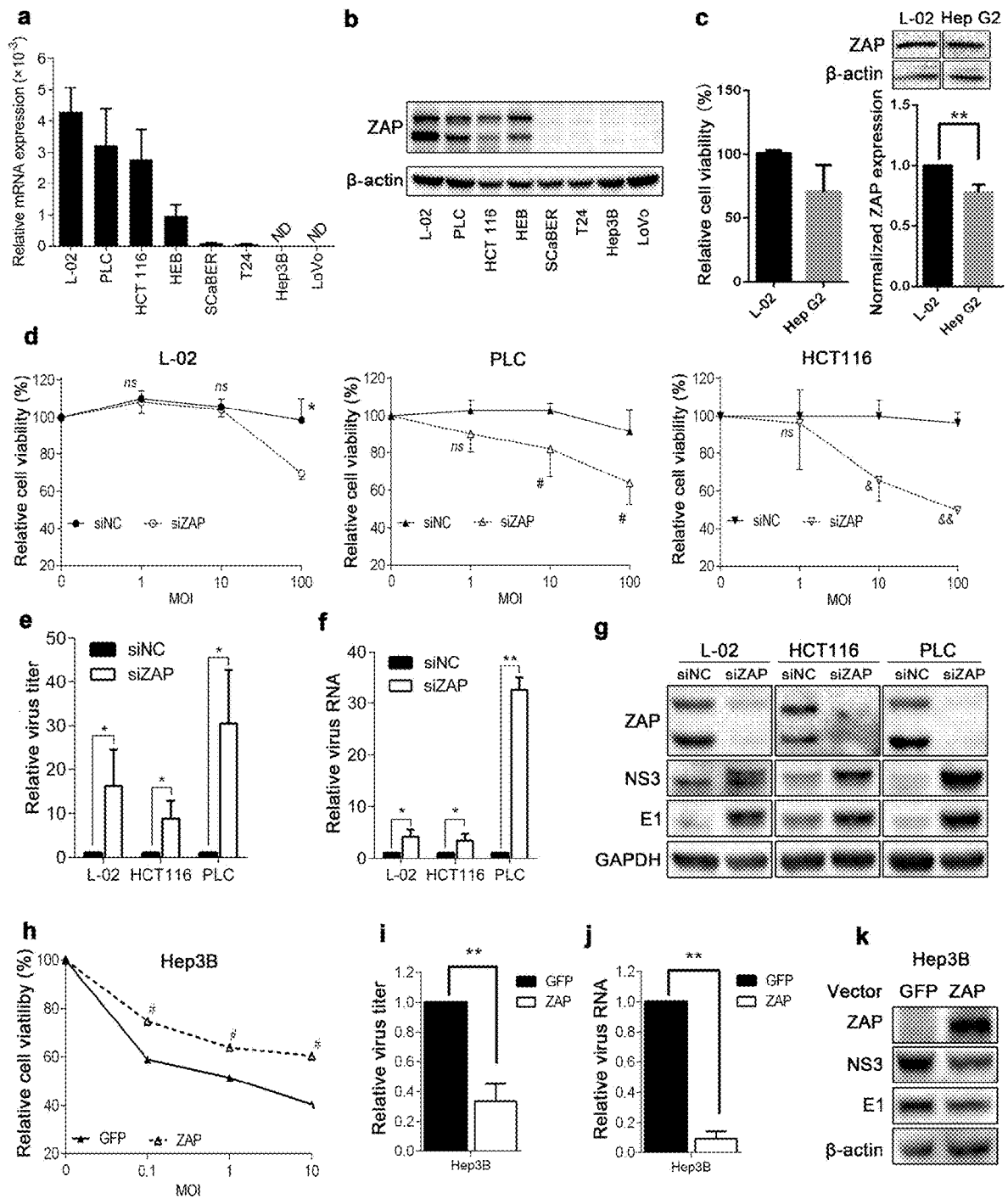

FIG. 3 shows that M1 virus selectively causes cell death of ZAP low expression/ZAP negative tumors;

a) shows differential expression of ZAP mRNA expression quantity in different cells; and ND represents that mRNA expression of ZAP is not detected;

b) shows differential expression of ZAP protein expression quantity in different cells; and β-actin is an internal reference;

c) shows the ZAP protein level in cells and the change of cell survival rate caused by the M1 virus infection. β-actin is the internal reference. statistical analysis of student's test is conducted. ** P<0.01;

d) shows that for normal cell L-02, tumor cell PLC and HCT116, after the knockdown of ZAP, cell death was induced significantly by M1 virus. The hollow circles/hollow triangles/hollow inverted triangles represent for the groups with interference knockdown of ZAP, the solid circles/solid triangles/solid inverted triangles represent for the groups of negative control of messy code interference. Students't test was adopted for statistical analysis, */#/& represents for P<0.05, & & represents for P<0.01, and ns represents for no statistical difference;

e) shows that for normal cell L-02, tumor cell PLC and HCT116, after the knockdown of ZAP, relative titer of the M1 virus is increased. Students't test was adopted for statistical analysis, and * represents for P<0.05;

f) shows that for normal cell L-02, tumor cell PLC and HCT116, after the knockdown of ZAP, the M1 virus RNA expression is increased. Students't test was adopted for statistical analysis, * represents for P<0.05, and ** represents for P<0.01;

g) shows that for normal cell L-02, tumor cell PLC and HCT116, after the knockdown of ZAP, the M1 virus protein NS3 and E1 expression are increased. GAPDH is used as the internal reference;

h) shows that an overexpression of ZAP partially block tumor cell death caused by M1 virus. Students't test was adopted for statistical analysis. # represents for P<0.05, and ns represents for no statistical difference;

i) shows that for tumor cells with an overexpression of ZAP, the relative titer of M1 virus is reduced. Students't test was adopted for statistical analysis. ** represents for P<0.01;

j) shows that for tumor cells with an overexpression of ZAP, the M1 virus RNA is reduced. Students't test was adopted for statistical analysis. ** represents for P<0.01;

k) shows that for tumor cells with an overexpression of ZAP, the expression of protein NS3 and E1 of the M1 virus is increased. β-actin is used as the internal reference.

Figure 4:
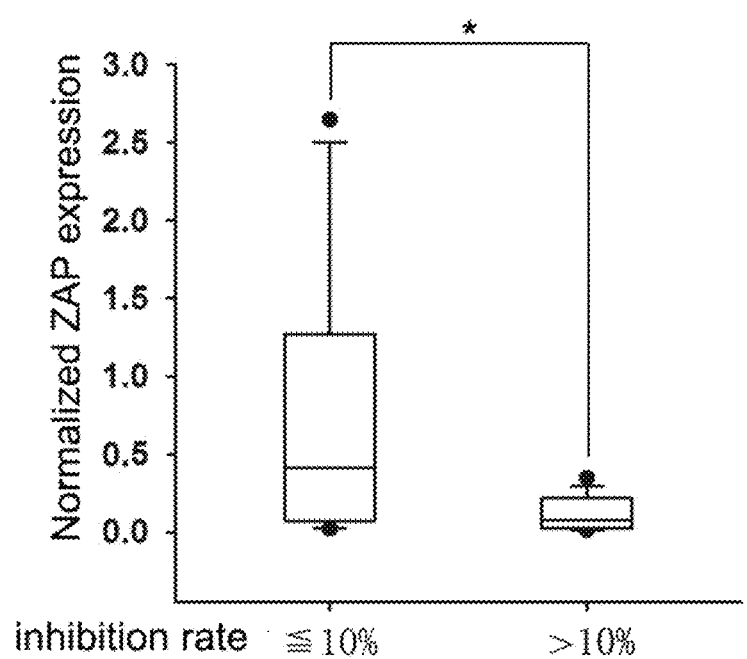

FIG. 4 shows that the inhibition rate of M1 virus against human ex vivo living tumor tissue is negatively correlated with ZAP mRNA expression level; ZAP mRNA expression is determined by QRT-PCR. The ZAP relative expression quantity of the M1 virus ineffective group (inhibition rate≤10%) is compared with that of M1 virus effective group (inhibition rate>10%). For those tumor tissues in which the inhibition rate of M1 virus treatment is less than or equal to 10%, the median of the ZAP normalized expression quantity is 0.414. For those tumor tissues in which the inhibition rate of M1 virus treatment is more than 10%, the median of the ZAP expression quantity is 0.075. Rank-sum test was adopted for statistical analysis adopts, P<0.05.

Figure 5:
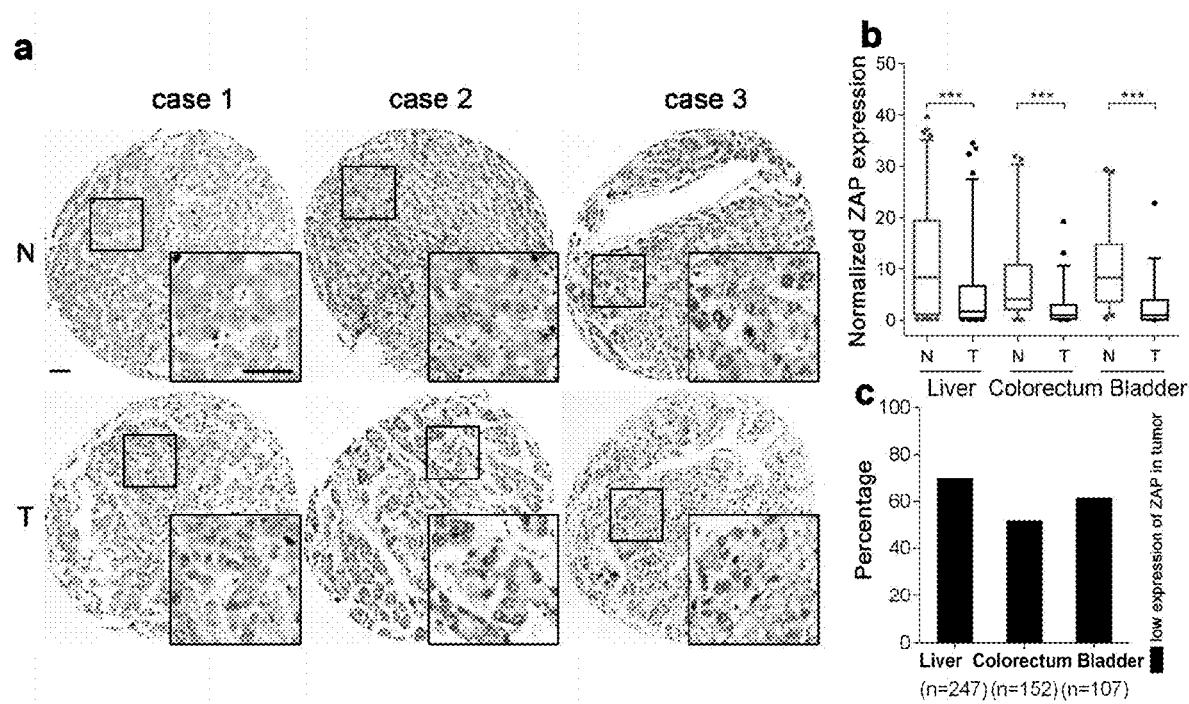

FIG. 5 shows a low expression of ZAP in various types of clinical pathological tumor tissues;

a) shows expressions of ZAP in clinical pathological tumor tissues by immunohistochemical staining detection; N: paracancerous non-neoplastic group, T: tumor group;

b) shows that in various types of tumor clinical pathological tissues, the ZAP expression in the tumor group is significantly lower than that in the paracancerous non-neoplastic group; N: the paracancerous non-neoplastic group, T: the tumor group; N and T adopt rank-sum test was adopted for statistical analysis, *** P<0.001;

c) shows that in various types of clinical pathological tumor tissues, the ZAP expression of the tumor tissues is lower than that in the paracancerous non-neoplastic tissues.

DETAILED DESCRIPTION OF THE EMBODIMENTS

The present disclosure is further illustrated by the following embodiments. However, embodiments of the present disclosure are not limited to the following description of the examples. Equivalent changes or adaptations made according to the principle or idea of the present disclosure should be deemed as within the protection scope of the present invention.

The materials and experiment methods used in the present disclosure are conventional materials and methods, unless otherwise specified.

Example 1. M1 Virus Selectively Caused Tumor Cells Death

1) M1 virus significantly causes morphological change of tumor cell

Materials:

Hepatocellular carcinoma Hep3B, human bladder transitional cell carcinoma T24, human colorectal cancer LoVo, human immortalized normal liver cell line L-02, M1 virus, high glucose DMEM medium, F-12 medium, inverted phase contrast microscope.

Methods:

a) Cultivation of cells: human hepatocellular carcinoma cell line Hep3B, human bladder transitional cell carcinoma cell line T24, and human immortalized normal liver cell line L-02 were grown in a DMEM complete medium containing 10% FBS, 100 U/ml penicillin and 0.1 mg/ml streptomycin; the human colorectal cancer cell line LoVo was grown in a F-12 complete medium containing 10% FBS, 100 U/ml penicillin and 0.1 mg/ml streptomycin. The cell lines were all placed in a 5% $CO_2$, 37☐constant temperature closed incubator (relative humidity 95%) for subculture. Growth of the cell lines was observed with the inverted microscope. Cells are passaged about every 2-3 days, and the cells in exponential growth phase were extracted for a formal experiment.

b) Observation under the cell microscope: the cells in exponential growth phase were selected, and added into a DMEM or F-12 complete medium (containing 10% fetal bovine serum, 1% double antibody) to prepare a cell suspension. The cells were inoculated into a 24-well culture plate at a density of $2.5 \times 10^4$/well. After 48 hours from the infection treatment with M1 virus (MOI=1), cytomorphological changes were observed under the inverted phase contrast microscope.

Figure 1:
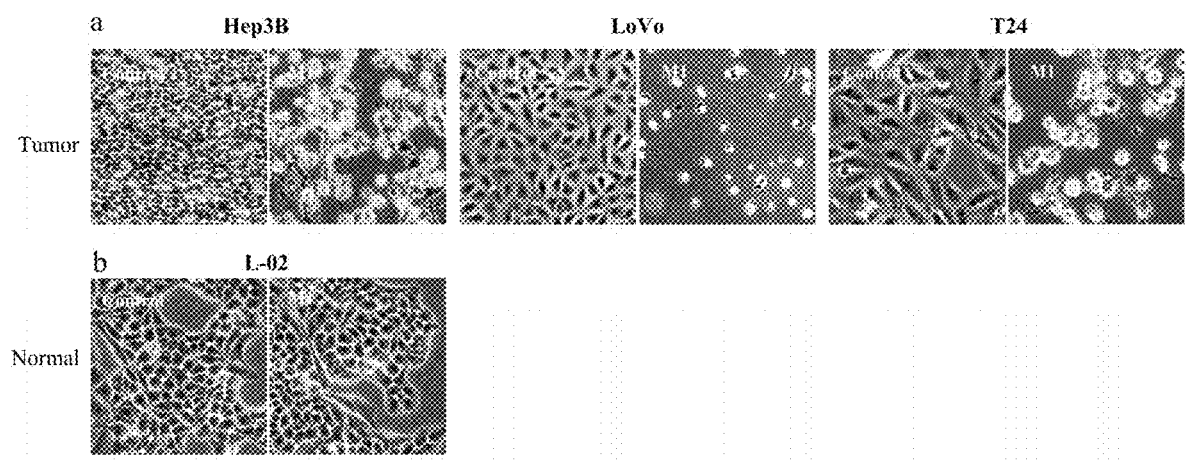
FIG. 1 shows that M1 virus significantly causes cytopathic effect of the tumors.

Results:

The cytomorphology was observed under the phase-contrast microscope. Hep3B cell, T24 cell and LoVo cell were all of adherent monoculture growth, and the cells were closely arranged, and the phenotypes were uniform. However, after 48 hours from the M1 virus (MOI=1) treatment, the morphology of the cells were obviously altered. Compared with the cells in the control group, the cell number in the viral infection group was obviously deceased. The cell body was contracted to a spherical shape, and its refractive index was obviously increased, presenting a death pathological change, as shown in FIG. 1a. FIG. 1b shows effect of the M1 virus infection on the normal cells. L-02 cells were infected by M1 virus with the equal titer, and no obvious change in cell number and morphology was found. The results indicate that M1 virus selectively caused cell death of tumor cells, but had no effect on the survival of the normal cells.

2) M1 virus selectively reduced survival of the tumor cell lines

Materials:

Thirty four tumor cell lines (see Table 1), three human immortalized normal cell lines (see Table 1), M1 virus, high glucose DMEM medium, F-12 medium, MTT (tetramethyl thiazolyl tetrazolium).

Methods:

a) Inoculation of cells and administration treatment: the cells in the exponential growth phase were selected and added into the DMEM (or F-12) complete medium (containing 10% fetal bovine serum and 1% double antibody) to prepare a cell suspension, and inoculated into a 96-well culture plate at a density of $4 \times 10^3$/well. After 12 hours the cells were found completely adherent to the wall. The experiment was divided into an experiment group and a control group, the experiment group was M1 virus (MOI=10) infected cell; the control group was high glucose DMEM solvent control group. Five composite orifices were disposed in the two groups.

b) Reaction of MTT with succinate dehydrogenase in the cells: when cultured to 48 hours, MTT 15 µl (5 mg/ml) was added into each well, and the incubation was continued for 4 hours. By microscopic examination, granular blue and purple formazan crystal formed in the living cells were observed.

c) Dissolution of formazan particles: the supernatant was carefully sucked off, and DMSO 100 µl/well was added to dissolve the resulting crystal, then the resulting solvent was shook on a microoscillator for 5 minutes, and the optical density (OD value) of each well was detected on a enzyme linked detector at a wavelength of 570 nm. The experiments were repeated for 3 times in every group. Cell survival rate=OD value of drug treatment group/OD value of control group×100%.

Results:

As shown in Table 1, after 48 hours of tumor cell treatment with M1 virus (MOI=10), the cell death rate of pancreatic cancer, nasopharyngeal carcinoma, prostate cancer and melanoma were more than 50%; the cell death rate of colorectal cancer (LoVo, HCT-8, SW620 and SW480), liver cancer (Hep3B, Huh-7 and Huh-6), bladder cancer and breast cancer were more than 40%; the cell death rate of glioma, cervical cancer, lung cancer were more than 30%; the cell death rate of gastric cancer was more than 20%. There were no statistically significant changes in the cell survival rate of three normal cell lines (L-02, HEB and SV-HUC-1) as well as PLC and HCT116. The results indicated that the M1 virus infection selectively caused cell death in most of the tumors.

TABLE 1

M1 virus significantly reduced survival rate of tumor cells

| Cell lines | Source | Survival rate (%) | Statistical significance |
|---|---|---|---|
| Hep3B | Liver cancer | 3.8 | — |
| Huh-7 | Liver cancer | 52.2 ± 10.0 | ** |
| Huh-6 | Liver cancer | 59.0 ± 8.9 | ** |
| HepG2 | Liver cancer | 70.4 ± 3.5 | * |
| PLC | Liver cancer | 80.5 | — |
| HCT116 | Liver cancer | 81.3 ± 4.3 | ns |

TABLE 1-continued

M1 virus significantly reduced survival rate of tumor cells

| Cell lines | Source | Survival rate (%) | Statistical significance |
|---|---|---|---|
| LoVo | Colorectal cancer | 6.9 | — |
| HCT-8 | Colorectal cancer | 35.4 ± 5.2 | ** |
| SW620 | Colorectal adenocarcinoma | 43.7 ± 6.7 | ** |
| SW480 | Colorectal cancer | 53.8 ± 8.4 | ** |
| SCaBER | Bladder cancer | 11.5 ± 4.4 | ** |
| T24 | Bladder cancer | 21.1 ± 3.8 | ** |
| UM-UC-3 | Bladder cancer | 39.8 ± 19.6 | ** |
| 5637 | Bladder cancer | 50.2 ± 19.0 | ** |
| Capan-1 | Pancreatic cancer | 40.4 ± 10.1 | ** |
| PANC-1 | Pancreatic cancer | 49.3 ± 16.3 | ** |
| SW1990 | Pancreatic cancer | 45.6 ± 16.9 | ** |
| MIA PaCa-2 | Pancreatic cancer | 49.1 ± 13.2 | ** |
| U-87 MG | Malignant glioma | 32.4 | — |
| U-251 | Malignant glioma | 34.7 ± 4.9 | ** |
| T98G | Glioblastoma multiforme | 38.2 | — |
| U-138 MG | Malignant glioma | 40.1 | — |
| MGR2 | Glioma | 63.2 | — |
| MDA-MB-468 | Breast cancer | 43.7 ± 10.1 | ** |
| MDA-MB-231 | Breast cancer | 58.9 ± 2.7 | ** |
| C-33 A | Cervical cancer | 14.8 ± 1.8 | ** |
| HeLa | Cervical cancer | 66 | — |
| 22Rv1 | Prostate cancer | 39.1 | — |
| CNE-2 | Nasopharyngeal carcinoma | 24.5 | — |
| CNE-1 | Nasopharyngeal carcinoma | 48.2 | — |
| A-375 | Melanoma | 47.3 ± 19.2 | * |
| A549 | Lung cancer | 68.2 | — |
| NCI-N87 | Gastric cancer | 76.4 ± 9.3 | * |
| HGC-27 | Gastric cancer | 79.2 | — |
| L-02 | Normal liver cell | 100.3 ± 10.0 | ns |
| HEB | Glial cell | 98.8 | — |
| SV-HUC-1 | Oviductal epithelial immortalized cell | 97.2 | — |

(Note:
** $p < 0.01$,
* $p < 0.05$,
ns: the difference has no statistical significance.
Statistical methods: student's test,
—: no statistics).

Example 2. M1 Virus Selectively and Effectively Inhibited Tumor Growth

1) In tumor-bearing mice body, M1 virus effectively inhibiting tumor growth

Materials:

M1 virus, human liver cancer cell line Hep3B, human colorectal cancer cell line LoVo, fifty eight 4-week-old female BALB/c nude mice.

Methods:

a) Modeling of the tumor-bearing mice: $5 \times 10^6$ Hep3B or LoVo cells were dorsal subcutaneously injected into 4-week-old BALB/c nude mouse.

b) Intratumoral administration: when Hep3B tumor volume reached about 50 mm$^3$ or LoVo tumor volume reached about 70 mm$^3$, the intratumoral injection administration was initiated. The tumor was injected with M1 viruses for totally six times within 12 days ($2 \times 10^6$ PFU/time), and OptiPRO™ SFM medium injection treatment was set as solvent control group. Length and width of the tumor and body weight were measured every two days, and the volume of the tumor was calculated according to the formula: length×width$^2$/2.

c) Intravenous administration: when Hep3B cell tumor volume reached about 50 mm$^3$, it was intravenously injected with M1 virus ($3 \times 10^7$ PFU/time), and after three days, a second intravenous injection was administrated. OptiPRO™ SFM medium injection treatment was set as the solvent control group. The body weight and length and width of the tumor were measured every three days, and the volume of tumor was calculated according to the formula: length×width$^2$/2.

Results:

After subcutaneous tumor-bearing Hep3B (FIGS. 2a and 2c) and LoVo (FIG. 2b) nude mouse models were established on the BALB/c nude mouse, M1 viruses were administrated continuously for several times by intratumoral (FIG. 2a and FIG. 2b) or intravenous injection (FIG. 2c), and the changes of tumor volume and animal body weight of the nude mouse were observed. In the Hep3B nude mouse model, intratumoral injection administration was adopted as shown in FIG. 2a. At the 20$^{th}$ day the experiment was terminated, the mean value of tumor volume of the solvent control group was 0.368±0.051 cm$^3$, and the mean value of tumor volume of the M1 virus group was 0.172±0.058 cm$^3$. Statistic results indicated that M1 virus significantly inhibited tumor growth of the Hep3B tumor-bearing mice. In addition, there is no significant difference in average body weight between the M1 virus group nude mouse (16.4±1.54 g) and the control group nude mouse (17.0±1.16 g), and the mental status of the M1 virus group nude mouse were good, indicating a good safety of the M1 virus. In the LoVo nude mouse model, intratumoral administration was conducted as shown in FIG. 2b. The experiment was terminated at the 24$^{th}$ day, the mean value of tumor volume in the control group was 0.546±0.087 cm$^3$, and the mean value of tumor volume in the M1 virus group was 0.389±0.049 cm$^3$. Statistic results indicated that M1 virus significantly inhibited tumor growth of the LoVo tumor-bearing mice. In addition, there is no significant difference in average body weigh between M1 virus group nude mouse (18.9±1.40 g) and the control group nude mouse (19.4±1.86 g), and the mental status were good, indicating a good safety of the M1 virus; in the Hep3B nude mouse model, intravenous injection administration was conducted as shown in FIG. 2c. The experiment was terminated at the 21$^{st}$ day, the average tumor volume of the control group was 0.247±0.067 cm$^3$, and the average tumor volume in the M1 virus group was 0.134±0.057 cm$^3$. Statistic results indicated that M1 virus significantly inhibited tumor growth of Hep3B tumor-bearing mice. In addition, there is no significant difference in average body weight between the M1 virus group nude mouse (17.2±2.50 g) and control group (17.5±2.16 g), and the mental status were good, indicating a good safety of the M1 virus.

2) M1 virus was selectively enriched in the tumor tissue

Materials:

Twenty four 4-week old female BALB/c nude mice, liver cancer cell line Hep3B, Trizol, a tissue homogenizer, a real-time fluorescence quantitative PCR instrument.

```
β-actin primer:
Sense strand
(SEQ ID No. 1: GATCATTGCTCCTCCTGAGC)

Antisense strand
(SEQ ID No. 2: ACTCCTGCTTGCTGATCCAC)

M1 viral nonstructural protein NS1 primer:
Sense strand
(SEQ ID No. 3: GTTCCAACAGGCGTCACCATC)

Antisense strand
(SEQ ID No. 4: ACACATTCTTGTCTAGCACAGTCC)
```

Methods:

$5 \times 10^6$ Hep3B cells were dorsa subcutaneously injected into 4-week-old nude mice. After four days, each mouse was injected with M1 virus via tail vein ($3 \times 10^7$ PFU). After administration, the nude mice were killed respectively at 1, 2, 3 and 4 days, and the tissue samples were collected (including tumor, heart, liver, spleen, lung, kidney, brain, and muscle), and RNAs is tissues were extracted. Then, the quantity of the M1 virus was determined by QRT-PCR method, in order to determine the M1 virus non-structural protein NS1 representing the M1 virus quantity. In the meanwhile the β-actin internal reference was determined, and relative quantity of the M1 virus RNA was calculated according to formula: $2^{-(C_{t\text{-}NS1}-C_{t\text{-}internal\ reference})}$. The $C_{t\text{-}NS1}$ and $C_{t\text{-}internal\ reference}$ were from instrument reading in Applied Biosystems 7500 Fast Real-Time PCR System.

Results:

As shown in FIG. 2d, in the nude mouse subcutaneous Hep3B tumor model, at four different time points, the M1 virus quantity in the tumor tissues is $10^2$-$10^6$ times more than that in other organ tissues, indicating a selective enrichment of the M1 virus in the tumor tissues.

Example 3. M1 Virus Selectively Caused Cell Death in ZAP Low Expression/ZAP Negative Tumors M1 virus selectively caused cell death of the tumors with ZAP low expression, but had no effect on normal cells. It was indicated that the expression level of ZAP was the decisive factor of M1 virus selectivity. In normal cells and tumor cells with ZAP normal expression/high expression, by interfering RNA and knockdown of expression level of ZAP, the M1 virus could significantly cause cell death. Meanwhile, in the low ZAP expression tumor cell, by an overexpression of ZAP, the tumor cell death caused by the M1 virus was partially blocked.

1) M1 virus did not cause cell death of the normal cells and tumors with ZAP high expression.

Materials:

M1 virus, human liver cell L-02, human glial cell HEB, human bladder cancer cell SCaBER and T24, human liver cancer cell line Hep3B and PLC, human liver cancer cell line Hep G2, human colorectal cancer cell line LoVo and HCT116; Western bolt: cell total protein extract (M-PER® Mammalian Protein Extraction Reagent, Thermo), ZAP antibody (Thermo, USA), β-actin antibody (Neomarker, USA); Extracting RNA. PCR: RNA extraction reagent Trizol, a real-time quantitative PCR instrument, Applied Biosystems 7500 Fast Real-Time PCR System (Life, USA),

```
ZAP primer:
ZAP sense strand
(SEQ ID No. 5: TCACGAACTCTCTGGACTGAA)

ZAP antisense strand
(SEQ ID No. 6: ACTTTTGCATATCTCGGGCATAA)
```

β-actin primer is the same as Example 2.

Methods:

The cells in exponential growth phase were selected, and added into a DMEM or F-12 complete medium (containing 10% of fetal bovine serum and 1% of double antibody) to prepare a cell suspension, the cells were inoculated into a 35 mm well at a density of $2\times10^5$/well. RNA was extracted, and ZAP mRNA expression quantity in the cells was determined by PCR. The internal reference of this experiment was β-actin. ZAP mRNA normalized expression quantity was calculated according to the formula: ZAP normalized mRNA expression quantity=$2^{-(C_{t\text{-}NS1}-C_{t\text{-}internal\ reference})}$. The $C_{t\text{-}NS1}$ and $C_{t\text{-}internal\ reference}$ were from instrument reading of Applied Biosystems 7500 Fast Real-Time PCR System, and they represented for the cycle number corresponding to the threshold when the fluorescence signal began to enter the exponential growth stage from the background during PCR amplification.

The cell total protein was extracted, quantified, and a Western Blot experiment was conducted (electrophoresis, trarsmembrane, blocking, incubation of primary antibody and secondary antibody, and development). The ZAP and internal reference β-actin band grey scale were scanned by an imaging software Image Lab, the band grey scale was detected, and the ZAP normalized protein expression quantity was calculated according to the following formula: ZAP normalized protein expression quantity=ZAP band grey scale/internal reference band grey scale. The experiments were repeated for 3 times, and an average value was taken, to calculate the ZAP normalized protein expression quantity.

Results:

As shown in FIGS. 3a and 3b, in tumor cell SCaBER, T24, Hep3B and LoVo, mRNA (FIG. 3a) and protein (FIG. 3b) normalized expression quantity of the ZAP were almost undetectable, which was significantly lower than that in the normal cells (L-02 and HEB) and the tumor cells (PLC, HCT116).

The M1 virus caused cell death of ZAP low expression/negative tumor, but did not cause cell death of ZAP high expression tumor. There was no change of statistical significance in survival rate after the normal cells (L-02 and HEB) and a part of the tumor cells (PLC, HCT116) were infected by the M1 virus. The survival rate of L-02 was 100.3%, and HEB was 98.8% (Table 1). After infection with the M1 virus, the cell survival rate of tumor cell SCaBER, T24, Hep3B and LoVo were significantly reduced to T24 21.1%, SCaBER 11.5%, LoVo 6.9% and Hep3B 3.8% (Table 1).

As shown in FIG. 3c and Table 1, the ZAP protein normalized expression quantity of Hep G2 liver cancer cells is lower than that of L-02 normal cells, and the ratio of the two was 0.8. After the L-02 cell was infected by the M1 virus, survival rate was not obviously altered, while for the Hep G2 cell, after it was infected by the M1 virus, the survival rate was reduced to 70.4%. There was a statistical difference between these two types of cell. This further indicated that M1 virus selectively caused cell death of ZAP low expression tumor.

2) M1 virus significantly caused cell death of normal cells and tumors after a knockdown of ZAP level.

Materials:

M1 virus, human liver cell L-02, human liver cancer cell PLC, human colorectal cancer cell HCT116, ZAP RNA interference fragment, MTT (methyl thiazolyl tetrazolium), Lipofectamine™ RNAiMAX (invertrogen, USA) Western bolt: cell total protein extract (M-PER® Mammalian Protein Extraction Reagent, Thermo), ZAP antibody (Thermo, USA), M1 virus NS3 antibody (Beijing Protein Innovation), M1 virus E1 antibody (Beijing Protein Innovation), GAPDH antibody (CST, USA); Extracting RNA, PCR: Trizol, a real-time quantitative PCR instrument (Applied Biosystems 7500 Fast Real-Time PCR System), β-actin, and M1 virus non-structural protein NS1 primer being the same as Example 2:

ZAP interference fragment (Si RNA) designed for target sequence SEQ ID No. 7:
5' CCAAGAGTAGCACTTGTTA3'

Si RNA sense strand
(SEQ ID No. 8: 5'CCAAGAGUAGCACUUGUUA dTdT 3')

Si RNA antisense strand
(SEQ ID No. 9: 3' dTdT GGUUCUCAUCGUGAACAAU 5')

ZAP messy code interference fragment control (siNC): the nucleotide ratio of sense strand and antisense strand is the same as that of Si RNA fragment, but order of arrangement is completely random.

Methods:

The cells in the exponential growth phase were selected, and added into a DMEM complete medium (10% fetal bovine serum, 1% double antibody) to prepare a cell suspension, and the cells were inoculated into a 6-well plate at a density of $1\times10^5$/well. After 24 hours, Si RNA fragment wrapped with RNAiMAX was added. After 48 hours, cells were infected with the M1 virus. After 48 hours of the infection, the specimens were treated.

MTT 20 μl (5 mg/ml) was added into each well, and after four hours, the absorbance value was determined, and cell survival rate was calculated. The siZAP experiment group was treated with the ZAP RNA interference fragment, and the siNC control group was treated by ZAP messy code interference fragment.

a) The cell supernatant was collected, and the virus titer was detected by TCID50 method.

b) RNA specimens were extracted, performed with PCR, and the M1 virus quantity was determined by detecting a quantity of M1 virus non-structural protein NS1. β-actin was the internal reference.

c) The protein specimen was extracted, ZAP protein expression and M1 virus protein NS3 and E1 were detected by Western blot, and the internal reference was GAPDH. The calculation of the ZAP normalized expression quantity was the same as 1) of Example 3 except that β-actin is replaced by GAPDH as the internal reference).

d) The experiment was repeated for 3 times, the data was represented by mean value±standard deviation; student's test statistics was conducted by comparing with respective control groups, */#/& represented P<0.05, **/& & represented P<0.01, ns represented no statistical difference.

Results:

As shown in FIG. 3d-3g, after human normal liver cell L-02, human liver cancer cell PLC and human colorectal cancer cell HCT116 were treated with ZAP RNA interference fragment, ZAP protein expression quantity was significantly reduced to an undetectable level (FIG. 3g), while M1 virus protein NS3 and E1 protein were obviously increased; after an infection with M1 virus (MOI=100), the survival rate of the L-02 cell (siZAP group) with a knockdown of ZAP level was significantly reduced to 69.7%±3.45%, the survival rate of PLC cell with a knockdown of ZAP level was reduced to 63.9%±11.5%, and the survival rate of HCT116 cell with a knockdown of ZAP level was reduced to 49.6%±1.21% (FIG. 3d); as shown in FIG. 3e, after 48 hours of infection with the M1 virus, the relative M1 virus titer in the L-02 cell with a knockdown of ZAP (siZAP group) was of 4.10±1.38 times of that in the corresponding siNC group; while for HCT116 cell (siZAP group), it was of 3.39±1.27 times of that in the corresponding siNC group; while for PLC cell (siZAP group), it was of 32.6±2.34 times of that in the corresponding siNC group. Meanwhile, as shown in FIG. 3f, after 48 hours of infection with the M1 virus, the M1 virus RNA expression quantity in the L-02 cell with a knockdown of ZAP (siZAP group) was of 16.3±8.20 times of that in the corresponding siNC group; while for HCT116 cell, it was of 8.82±4.02 times of that in the corresponding siNC group; while for PLC cell, it was of 30.5±12.23 times of that in the corresponding siNC group. The above results indicated that M1 virus significantly caused normal cell and tumor cell death after a knockdown of the ZAP level.

3) tumor cell death induced by M1 virus was antagonized by an overexpression of ZAP.

Materials:

M1 virus, human liver cancer cell Hep3B, pReceiver-M02-GFP plasmid for expressing GFP (blank control plasmid, Guangzhou Funeng Gene Co., Ltd.), pReceiver-M02-ZAP plasmid for expressing ZAP (overexpressed ZAP plasmid), FuGENE HD transfection reagent, MTT (methyl thiazolyl tetrazolium)

Extracting RNA, PCR: Trizol, a real time quantitative PCR instrument (Applied Biosystems 7500 Fast Real-Time PCR System), β-actin, M1 virus non-structural protein NS1 primer being the same as Example 2.

Western bolt: cell total protein extract (M-PER® Mammalian Protein Extraction Reagent, Thermo), ZAP antibody (Thermo, USA), M1 virus NS3 antibody (Beijing Protein Innovation), M1 virus E1 antibody (Beijing Protein Innovation), GAPDH antibody (CST, USA).

Methods:

The cells in exponential growth phase were selected, and added into DMEM complete medium (10% of fetal bovine serum and 1% of double antibody) to prepare a cell suspension, then the cells were inoculated in a 6-well plate at a density of $1\times10^5$/well. After 24 hours, the cells were the transfected with overexpressed GFP control plasmids and ZAP overexpression plasmids, respectively, to obtain the corresponding cells expressing green fluorescent protein and the cells of ZAP overexpression. After 48 hours, the infection treatment with M1 virus was performed. After 48 hour of infection, the specimen was treated and detected.

a) The cell survival rate was determined by MTT method. MTT 20 μl (5 mg/ml) was added into each well, and after four hours, the absorbance value was detected at wavelength of 570 nM. Other treatments conducted were the same as Example 1.

b) The cell supernatant was collected, and the virus titer was detected by TCID50 method.

c) Total RNA specimen of the sample was extracted, and the RNA expression quantity of M1 virus was determined by QRT-PCR method, and calculated according to the method of Example 2.

d) The protein specimens were collected, ZAP protein expression quantity and M1 virus protein NS3, E1 protein expression quantity were detected by Western blot, and the treatment method was the same as 1 of Example 3).

e) Each experiment was repeated for three times, and the data were represented by mean value±standard deviation. Student's test was adopted for statistics by comparing with corresponding control groups. # represented for P<0.05, ** represented for P<0.01, and ns represented for the difference has no statistical significance.

Results:

As shown in FIG. 3k, after the human liver cancer cell Hep3B was transfected with the ZAP overexpression plasmid, the grey scale of the ZAP and the internal reference β-actin band in different specimens were scanned by Image Lab software, and respective ZAP normalized protein expression quantities were calculated. The ZAP normalized protein expression quantity in the ZAP overexpression group was 1.61±0.05, while in the overexpressed GFP control group it was 0.03±0.01. The mean value of the former was of 53.7 times of that of the latter; M1 virus protein NS3 and E1 protein were obviously increased;

As shown in FIG. 3h, an overexpression of ZAP partially blocked Hep3B cell death caused by M1 virus infection. After 48 hours of the infection by using different M1 virus titers, when MOI=0.1, the mean value of cell survival rate in the overexpressed ZAP group was 74.7%±8.94%, which was significantly higher than the cell survival rate in the overexpressed GFP control group (59.0%±6.27%); when MOI=1, the mean value of the cell survival rate in the overexpressed ZAP group was 69.4%±6.95%, which was significantly higher than the cell survival rate in the overexpressed GFP control group (51.4%±5.31%); when MOI=10, the mean value of cell survival rate in the overexpressed ZAP group was 63.7%±6.04%, which was significantly higher than the cell survival rate in the overexpressed GFP control group (40.5%±3.19%);

As shown in FIG. 3i, after the infection treatment with the M1 virus, the relative virus titer in the Hep3B cell with overexpressed ZAP was of 31.5±11.6% of that in the corresponding overexpressed GFP control group. Meanwhile, after M1 virus infection treatment, the M1 virus RNA expression quantity in the Hep3B cell with overexpressed ZAP was of 9.5±4.7% of that in the corresponding overexpressed GFP control group.

Example 4. M1 Virus Inhibited the Growth of ZAP Low Expression Human Ex Vivo Living Tumor Tissue (Ex Vivo)

Materials:
DMEM high glucose medium, TECIA (Tissue Culture-MTT Endpoint Computer Image Analysis Chemo-sensitivity Test), β-actin and ZAP primer is same as 1) of Example 3.

Methods:
a) Culture of human ex vivo living liver cancer tissue and colorectal cancer tissue The ex vivo living tissue was obtained by surgical excision in Tumor Prevention Center of Sun Yat-sen University, stored at 4 □, and then sent to the laboratory within four hours for drug sensitivity test. All the cases were confirmed by a histopathology examination. Under sterile condition, the tumor tissue was taken out, and cut into tissue pieces with a diameter of 0.5-1 mm, placed onto a 24-well culture plate (4-6 pieces per well), and 1 ml DMEM medium was added into each well. After one hour of culture, a projection illuminated image of the tumor tissue piece was taken by an image analyzer specialized for drug sensitivity test. The area of the tumor piece was determined and compared (area, A), to analyze the inhibitory effect of the M1 virus against the human ex vivo living tumor tissue.

b) Drug treatment and tissue activity determination
The tumor tissue was cultured in a $CO_2$ cell incubator for 12 hours. After the status was stable, $10^7$ PFU of M1 virus and the positive control drug 5-fluorouracil (5-Fu, 10 mg/L) were added. After 96 hours of the infection treatment, MTT (5 mg/ml) was added at 50 μl/well, and cultured for 3 hours. A diffusion light illuminated image of the tumor tissue piece was then taken by an image analyzer specialized for drug sensitivity test, to determine the blue dyed area by formazan in the tumor piece in each well and the coloring degree (blue area, BA). Then the tissue survival rate (survival fraction, SF) was calculated according the following formula:

$$SF = \frac{BA_{drug\ treatment} / A_{drug\ treatment}}{BA_{control} / A_{control}} \times 100\%$$

Tumor tissue inhibition rate (Cell inhibition, CI): CI=(1-SF)×100%, $BA_{drug\ treated}$ represented for blue dyed area of M1 virus/5-Fu treated group, $A_{drug\ treated}$ represented for area of tumor piece of M1 virus/5-Fu treated group, $BA_{control}$ represented for blue dyed area of the solvent control treated group, and $A_{control}$ represented for the area of tumor piece in the solvent control treated group.

c) Determination of ZAP mRNA normalized expression quantity

According to a standard of tumor inhibition rate of 10%, all the above-mentioned case tissues were divided into two groups. The RNA of the specimens were respectively extracted, and levels of the ZAP mRNA and β-actin (internal reference) were determined by QRT-PCR method. The difference in ZAP normalized expression quantities between the two groups was compared. Rank-sum test was adopted for statistical analysis. The method for calculating the ZAP normalized expression quantity is the same as 1) of Example 3.

Results:
a) As shown in Table 2, for the liver cancer tissue, the ratio of cases with the inhibition rate more than 10% was 59.5% in the M1 virus group, which was higher than that in the 5-Fu group (53.8%). It was proved that the effectiveness rate of the M1 virus treatment was higher than the current 5-Fu drug treatment for clinical therapy for liver cancer.

TABLE 2

M1 virus and 5-Fu inhibiting the survival rate of human ex vivo living liver cancer tissues

| Inhibition rate (% control) | M1 virus treatment (%) | 5-Fu treatment (%) |
| --- | --- | --- |
| >10% | 22 (59.5%) | 14 (53.8%) |
| ≤10% | 15 (40.5%) | 12 (46.2%) |
| Number of cases | 37 | 26 | b) As shown in Table 3, for the colorectal cancer tissues, the ratio of cases in which the inhibition rate being more than 10% was 71.4% in the M1 virus group, which was higher than that in the 5-Fu group (61.5%). It was proved that the effectiveness rate of M1 virus treatment was higher than the current 5-Fu drug treatment for clinical therapy for colorectal cancer.

TABLE 3

M1 virus and 5-Fu inhibiting the growth of human ex vivo living colorectal cancer tissue

| Inhibition rate (% control) | M1 virus treatment (%) | 5-Fu treatment (%) |
| --- | --- | --- |
| >10% | 10 (71.4%) | 8 (61.5%) |
| ≤10% | 4 (28.6%) | 5 (38.5%) |
| Number of cases | 14 | 13 | c) The above-mentioned human ex vivo living tumor tissues which were treated by the M1 virus were divided into two groups according to an inhibition rate of 10%. The correlation of the ZAP mRNA expression level with the inhibition rate in these tissues was further analyzed. The ZAP normalized expression quantity of the group with a M1 virus treatment inhibition rate of more than 10% was 0.117±0.890, which was lower than that in the group with an inhibition rate of less than or equal to 10% (0.791±0.108). The ratio of the mean value of the two groups was 0.148. As shown in FIG. 4, the median of tumor tissue ZAP normalized expression quantity in the group with a M1 virus treatment inhibition rate of less than or equal to 10% was 0.414, and the median of tumor tissue ZAP expression quantity in the group with a M1 virus treatment inhibition rate of more than 10% was 0.075. Rank-sum test method was adopted for statistics. The difference had a statistical significance (P<0.05), indicating that the M1 virus could selectively cause tissue death in ZAP low expression/ZAP negative tumors.

Example 5. Low Expression of ZAP in Various Types of Tumor Clinical Pathological Tissues Materials:
Eight tissue chips from 506 patients (including liver cancer, colorectal cancer, bladder cancer and paired paracancerous tissue), ZAP antibody (Thermo, USA), and APERIO fully automatic digital pathology slice scanner.

Methods:
The eight tissue chips from multiple centers was subjected to Immunohistochemical staining (IHC), scanned by APERIO scanner, and the staining density was calculated with a matching software, to determine the ZAP normalized expression quantity. ZAP normalized expression quantity=ZAP staining intensity within visual field/cell numbers within visual field. The cell number within visual field was used as homogenization standard.

Results:
Using an immunohistochemical method, the inventors determined the ZAP expression in various types of human tumor pathological specimens. FIG. 5a showed representative mappings for immunohistochemical staining of ZAP in human liver cancer, colorectal cancer, and bladder cancer pathological tissue specimens. Staining results of ZAP in the tumor tissues were lighter than those in the corresponding paracancerous tissues.

As shown in FIG. 5b, statistical analysis for the mean value of the ZAP protein homogenize expression quantity in liver cancer, colorectal cancer, bladder cancer and corresponding paracancerous non-neoplastic tissues was conducted. The results indicated that the averaged ZAP protein normalized expression quantity in the above-mentioned each type of tumor tissues was significantly lower than that in the corresponding paracancerous non-neoplastic tissues, indicating a low expression of ZAP in the tumor tissues. The averaged ZAP normalized expression quantity in all liver cancer tumor tissues was 5.83±8.49, which was significantly lower than that in the corresponding paracancerous non-neoplastic tissues (11.8±11.5). The ratio of these two average values was 0.494. The averaged ZAP normalized expression quantity in all colorectal cancer tumor tissues was 2.41±3.60, which was significantly lower than that in the corresponding paracancerous non-neoplastic tissues (8.30±8.94). The ratio of these two average values was 0.290. The averaged ZAP normalized expression quantity of all the bladder cancer tumor tissues was 2.93±4.63, which was lower than that in the paracancerous non-neoplastic tissues (10.3±8.36). The ratio of these two average values was 0.284.

As indicated in FIG. 5c, within all the liver cancer cases analyzed, the case number of ZAP low expression was of a percentage of 69%. Within all the colorectal cancer cases analyzed, there was a percentage of 52% of cases with ZAP low expression. Within all the bladder cancer cases analyzed, there was a percentage of 61% of cases with ZAP low expression. ZAP becomes a selective molecular marker for M1 viral antitumor therapy for liver cancer, colorectal cancer and bladder cancer.

Example 6. Preparation Method of the M1 Virus

Materials:
African Green Monkey kidney cell Vero, high glucose DMEM medium, OptiPRO™ SFM medium (1x), M1 virus, 100 mm cell culture dish, centrifuger.

Methods:
The cells in the exponential growth phase were selected, and added into a DMEM complete medium (containing 10% fetal bovine serum and 1% double antibody) to prepare a cell suspension. Then the cells were inoculated into a 100 mm cell culture dish. When a cell fusion degree reached 80%-90%, the medium was replaced with OptiPRO™ SFM medium. Then, 50 μl (MOI=0.01) M1 virus was added for infection treatment. When a large area of pathological changes occurred in the cell (about 36 hours), the cell supernatant was collected. The cell supernatant was centrifuged at 2000-3000 RPM for 5 minutes, then the supernatant was carefully sucked out, mixed and subpackaged, and stored at a −80□ refrigerator.

The above-described examples are illustration of the exemplary embodiment and effect of the present disclosure. However, the embodiment of the present disclosure is not limited to the above-described examples. Any other change, modification, substitution, combination, and simplification without departing from the spirit and principle of the present disclosure are all included in the protection scope of the present disclosure.

The invention claimed is:

1. A method of treating a human subject with a tumor, comprising administering to the subject at least one alphavirus, wherein said alphavirus is an M1 virus; and
wherein said tumor is selected from the group consisting of liver cancer, colorectal cancer, bladder cancer, breast cancer, cervical cancer, prostate cancer, glioma, melanoma, pancreatic cancer, nasopharyngeal carcinoma, lung cancer, and gastric cancer.

2. A method of treating a subject with a tumor, comprising administering to the subject at least one alphavirus, wherein
the alphavirus is selected from an M1 virus and a Getah virus; and
the tumor is a ZAP low expression tumor or ZAP negative tumor.

3. The method of claim 1, wherein the tumor is a solid tumor.

4. The method of claim 1, wherein the tumor is selected from the group consisting of liver cancer, colorectal cancer, bladder cancer, breast cancer, cervical cancer, prostate cancer, glioma, melanoma, pancreatic cancer, nasopharyngeal carcinoma, and lung cancer.

5. The method of claim 1, wherein the tumor is selected from the group consisting of liver cancer, colorectal cancer, bladder cancer, breast cancer, cervical cancer, prostate cancer, melanoma, pancreatic cancer, nasopharyngeal carcinoma, lung cancer, and gastric cancer.

6. The method of claim 1, wherein the alphavirus is administrated by injection or orally.

7. The method of claim 1, wherein said alphavirus is selectively enriched in tumor tissue after administration.

8. The method of claim 1, wherein a ZAP inhibitor is administrated during or prior to the administration of said alphavirus.

9. The method of claim 8, wherein the ZAP inhibitor is selected from ZAP expression inhibitor and function inhibitor.

10. The method of claim 8, wherein the ZAP inhibitor is selected from ZAP interference fragment and ZAP antibody.

11. The method of claim 1, wherein before administrating, the subject is subjected to the detection of tumor ZAP expression level, and,
  a) if the tumor is of ZAP low expression or ZAP negative expression, said alphavirus is directly administrated;
  b) if the tumor is of ZAP normal expression/ZAP high expression, a ZAP inhibitor is provided before or during the administration of the M1 virus.

12. The method of claim 11, wherein the ZAP inhibitor is a tumor targeted ZAP inhibitor.

13. The method of claim 1, wherein the genome of said at least one alphavirus has at least 97.8% nucleotide sequence identity to the genome of the M1 virus deposited under Accession No. CCTCC V201423.

14. The method of claim 1, wherein the tumor is selected from the group consisting of liver cancer, colorectal cancer, bladder cancer, breast cancer, prostate cancer, melanoma, pancreatic cancer, and nasopharyngeal carcinoma.

15. The method of claim 1, wherein the tumor is selected from the group consisting of prostate cancer, melanoma, pancreatic cancer, and nasopharyngeal carcinoma.

16. The method of claim 1, wherein the tumor is selected from the group consisting of liver cancer and colorectal cancer.

17. The method of claim 1, wherein the alphavirus is administrated by injection.

18. The method of claim 1, wherein the alphavirus is administrated by intravenous injection or intratumoral injection, wherein:
  a) in the intratumoral injection, $2 \times 10^5$ PFU/kg-$2 \times 10^9$ PFU/kg is administrated every day; or
  b) in the intravenous injection, $2 \times 10^6$ PFU/kg-$2 \times 10^{10}$ PFU/kg is administrated every day.

19. The method of claim 8, wherein a ZAP inhibitor is administrated during or prior to the administration of said alphavirus.

20. The method of claim 1, wherein the genome of said at least one alphavirus is the genome of the M1 virus deposited under Accession No. CCTCC V201423.

* * * * *